(12) United States Patent
Jin et al.

(10) Patent No.: US 6,284,375 B1
(45) Date of Patent: Sep. 4, 2001

(54) LIPID VESICLE SYSTEM

(76) Inventors: Tuo Jin, 35 Charles Street West, #1102, Toronto, Ontario (CA); Peter Pennefather, 87 Earl Grey Road, Toronto, Ontario (CA), M5S 2S2; Ping I. Lee, 312 Pine Tree Rd., Radner, PA (US) 19087

( * ) Notice: Subject to any disclaimer, the term of this patent is extended or adjusted under 35 U.S.C. 154(b) by 0 days.

(21) Appl. No.: 08/953,552

(22) Filed: Oct. 17, 1997

Related U.S. Application Data

(60) Provisional application No. 60/028,828, filed on Oct. 18, 1996.

(51) Int. Cl.[7] ............................. B32B 5/16; A61K 51/12; A61K 9/133

(52) U.S. Cl. ..................... 428/403; 424/1.21; 424/1.29; 424/450; 424/484; 424/486; 424/489; 424/490; 424/491; 424/497; 424/498; 428/407

(58) Field of Search ................................. 428/403, 407; 424/1.21, 1.29, 450, 484, 486, 489, 490, 491, 497, 498

(56) References Cited

U.S. PATENT DOCUMENTS

| | | | |
|---|---|---|---|
| 4,438,052 | * 3/1984 | Weder et al. ................... 264/4.6 |
| 5,064,655 | * 11/1991 | Uster et al. ................... 424/450 |
| 5,340,588 | 8/1994 | Domb ........................... 424/450 |
| 5,464,629 | * 11/1995 | Monshipouri et al. .......... 424/450 |
| 5,498,420 | * 3/1996 | Mentrup Edgar et al. ....... 424/450 |
| 5,531,925 | * 7/1996 | Landh et al. ................. 252/299.01 |
| 5,614,222 | 3/1997 | Kaplan ......................... 424/489 |
| 5,833,647 | * 11/1998 | Edwards ....................... 604/22 |
| 5,837,221 | * 11/1998 | Bernstein et al. ............. 428/9.52 |
| 5,853,753 | * 12/1998 | Maierhofer et al. ............ 424/450 |
| 5,942,558 | * 8/1998 | Korb ........................... 523/106 |
| 5,955,096 | * 9/1999 | Santos et al. ................. 424/434 |
| 5,993,852 | * 11/1999 | Foldvari et al. .............. 424/450 |

OTHER PUBLICATIONS

Bayerl, T. M. and Bloom, M. (1990) Biophys. J., 58, 357–362.
Cai, S. J., McAndrew, C. S., Leonard, B. P., Chapman, K. D. and Pidgeon, C. (1995) J. Chromatogr. A 696, 49–62.
Chang, T. M. S. (1992) Biomat. Art. Cells & Immob. Biotech. 20, 159–179.
Gao, K. and Huang, L. (1987) Biochim. Biophys. Act, 897, 377–383.
McConnell, H. M., Watts, T. H. Weis, R. M. and Brian, A. A. (1986) Biochim. Biophys. Acta, 864, 95–106.
Ong, S. Liu, H. Qiu, X. Bhat, G. Pidgeon, C. (1995) Anal. Chem. 67, 755–762.
Plant, A. L. (1993) Langmuir, 9, 2764–2767.
Rogers, J. A. and Choi, Y. W. (1993) Pharm. Res. 10, 913–917.
Rothe, U., Aurich, H., Engelhard, H. and Oesterhelt, D. (1990) FEBS Lett. 263, 308–312.
Sackman, E. (1996) Science, 271, 43–48.
Spinke, J., Yang, J., Wolf, H., Liley, M., Ringsdorf, H. and Knoll, W. (1992) Biophys. J., 63, 1667–1671.

\* cited by examiner

*Primary Examiner*—Hoa T. Le
(74) *Attorney, Agent, or Firm*—Bereskin & Parr; Micheline Gravelle

(57) ABSTRACT

A novel lipid vesicle system is described. This system consists of a lipid shell that is anchored on the surface of a polymer matrix. The system has potential applications in drug delivery, drug targeting, protein separation, enzyme immobilization and blood cell substitution.

15 Claims, 4 Drawing Sheets

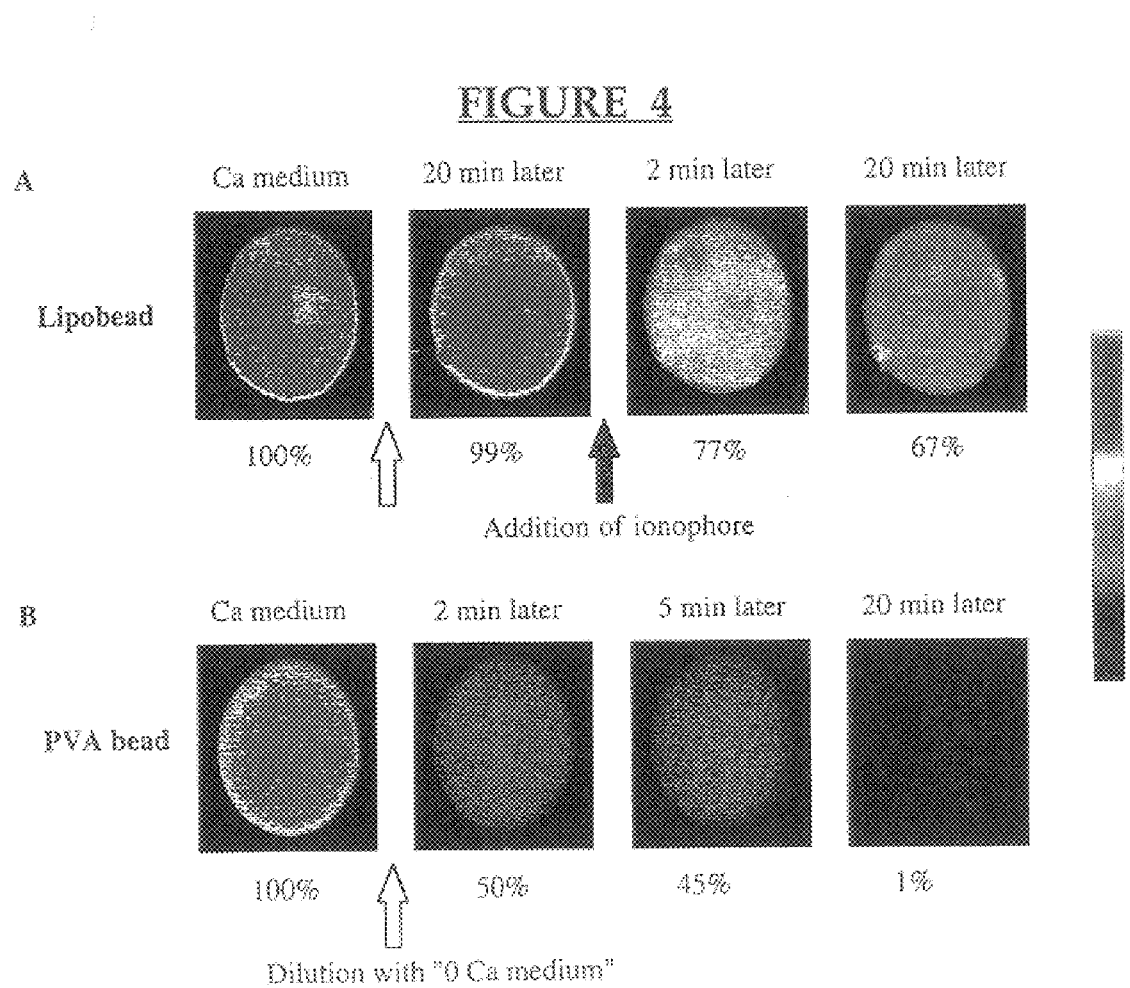

LIPID VESICLE SYSTEM

This application claims benefit from U.S. provisional application Ser. No. 60/028,828 filed on Oct. 18, 1996.

FIELD OF THE INVENTION

The present invention relates to a lipid vesicle system that is useful in a variety of biomedical applications including drug delivery, vaccine targeting, drug distribution and uptake, membrane protein reconstitution, enzyme immobilization and construction of artificial cells such as blood cells.

BACKGROUND OF THE INVENTION

Artificial particulate systems such as polymeric beads and liposomes are finding a variety of biomedical applications in drug delivery, drug targeting, protein separation, enzyme immobilization and blood cell substitution (1–6). Liposomes have a flexible, cell-like lipid bilayer surface which acts as a permeability barrier such that compounds can be entrapped in their aqueous interior. However, liposomes can be mechanically unstable and their loading capacity limited by the water solubility of the material to be loaded (7). Polymeric beads, although mechanically more stable and having a larger loading capacity then liposomes, lack many of the useful surface properties of a lipid bilayer shell.

Lipid bilayers supported on various solid surfaces, such as glass (8), plastic (5), and metal (9) as well as modified polymers (10) have previously been shown to provide a stable and well defined cell membrane-like environment that has found a number of basic and applied uses (11,12). Gao and Huang reported that encapsulation of hydrogel particles into liposomes enhanced the loading capacity and overall mechanical strength of the liposomal structure (13). However, in that system the unanchored bilayer is still somewhat unstable and the system could only be formed with specific lipid mixtures and only with polymer cores of certain sizes and shapes. The inventors have developed a hydrogel anchored lipid vesicle in which these limitations have been overcome.

SUMMARY OF THE INVENTION

The present inventors have developed a new hybrid lipid vesicle system with structural similarity to natural cells that combines complementary advantages of liposomes and polymeric beads. The system consists of a lipid shell that is anchored on the surface of a polymer matrix which acts like a cytoskeleton. Anchoring is provided by fatty acids covalently attached to the surface of the polymer matrix. These hydrophobic chains drive spontaneous assembly of a lipid shell on the modified polymer matrix when exposed to a suspension of liposomes. The bilayer is stable and acts as a permeability barrier to any compound loaded onto the polymer matrix. Lipid mobility in the shell is similar to that found in other unanchored lipid bilayers. The system has potential application in drug delivery and for functional reconstitution of membrane proteins.

Broadly stated, the present invention relates to a lipid vesicle composition comprising a lipid shell attached to a polymer matrix. Preferably, the lipid shell is covalently attached to the polymer matrix.

The invention also contemplates a method for preparing a lipid vesicle composition comprising:

(a) providing a modified polymer matrix having hydrophobic functional groups covalently attached to the polymer matrix; and (b) mixing the modified polymer core with a lipid suspension to form an anchored lipid shell on the matrix.

Other objects, features and advantages of the present invention will become apparent from the following detailed description. It should be understood, however, that the detailed description and the specific examples while indicating preferred embodiments of the invention are given by way of illustration only, since various changes and modifications within the spirit and scope of the invention will become apparent to those skilled in the art from this detailed description.

BRIEF DESCRIPTION OF THE DRAWINGS

FIG. 4 shows the fluorescent confocal images of lipobeads and bare beads.

DETAILED DESCRIPTION OF THE INVENTION

Lipid Vesicle Composition

Figure 1:
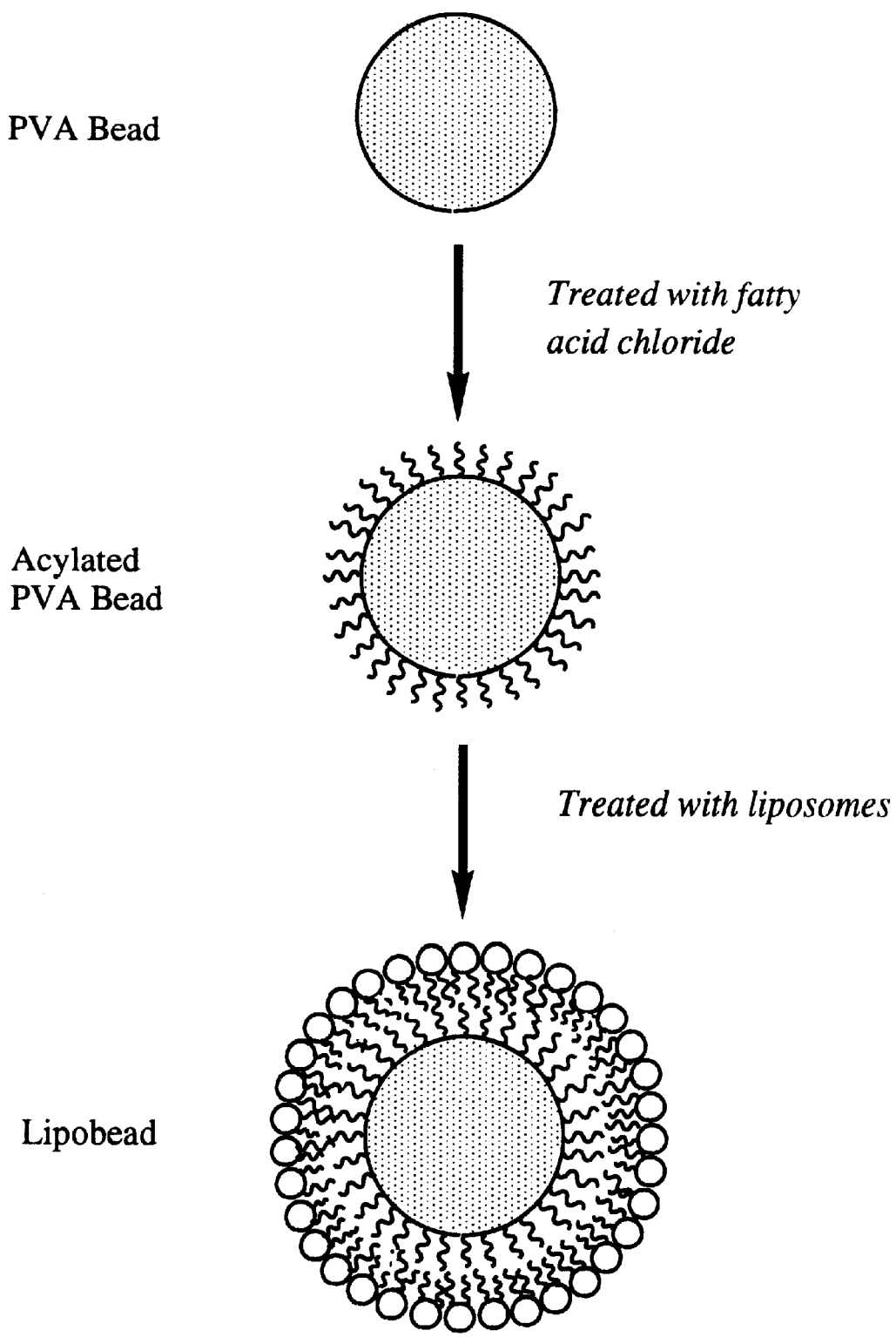
FIG. 1 is a schematic drawing showing the lipobead preparation.

As hereinbefore mentioned, the present invention relates to a lipid vesicle composition comprising a lipid shell attached to a polymer matrix.

The polymer matrix can be selected from any material and is preferably biodegradable, stable in physiological environments and suitable for human consumption. Examples of suitable matrix materials include, but are not limited to, polyvinyl alcohol (PVA) hydrogels, polysaccharides such as dextran, inulin, starch, chitin, xanthan gum, albumin and hydroxyether starches.

The matrix can be any shape including spheres, tubes, rings, strings or sheets. In one embodiment, the matrix is a hydrogel bead and the resulting lipid vesicle is a lipobead. The hydrogel beads of the invention have a diameter of between about 0.5 micrometers and about 500 micrometers.

The environment of the hydrogel core may be modified in various ways by modifying the properties of the aqueous solution used to swell the hydrogel (e.g. pH, osmolarity, excipient content etc.) or by modifying the hydrogel polymer (e.g. cross-link density, chemical modification etc.).

The lipid layer or shell can consist of any lipid material including lipids found in naturally occurring cell membranes and those that can form lipids.

As used herein the term "lipid material" includes fatty acids, whether saturated or unsaturated, such as monobasic aliphatic carboxylic acids which form esters with glycerol or other alcohols to make fats, oils, waxes and other lipids. Also included are the esters and ethers of glycerides, the esters formed by reaction of the fatty acids with glycerol, such esters formed from pharmaceutically acceptable weak acids such as tartaric acid and its diacetyl derivative, acetic acid ascorbic acid and citric acid, or one having a monophosphate group to yield the monophosphate ester. Suitable ethers are formed by reaction of the mono- or diglyceride with a functionally reactive lower alkyl, alkenyl, alkynyl, aryl or substituted aryl group to produce the corresponding pharmaceutically acceptable ether, as is known in the art. Polyhydric alcohols such as octanol or a carbohydrate polyol, e.g., sucrose, are also useful in the present invention.

In a preferred embodiment, the lipid material consists of liposomes. Liposomes may be constructed from one or more lipids so that they are small unilamellar vesicles, large unilamellar vesicles or oligolamellar vesicles.

The lipid shell acts as a permeability barrier to the compound contained in or on the polymer material. The release rate of the compound may be controlled by the type of lipid selected in generating the shell. The lipids can vary according to their charge, chain length and phase transition temperature.

Polymers matrices of the invention, such as hydrogel beads, may be loaded with a drug or therapeutic agent using techniques known in the art. The inventors have shown that the release of a compound from a hydrogel bead containing a lipid shell is much slower than the release from a bead without a shell. Therefore, the lipid vesicle composition of the present invention provides an improved delayed release vehicle for the delivery of therapeutic agents.

Process for Preparing Lipid Vesicle Composition

The invention also contemplates a method for preparing a lipid vesicle composition comprising:
(a) providing a modified polymer matrix having hydrophobic functional groups covalently attached to the polymer matrix; and
(b) mixing the modified polymer core with a lipid suspension to form a lipid shell on the matrix.

The modified polymer matrix should be modified with a sufficient density of hydrophobic molecules that can insert into the leaflet of the lipid shell and thereby promote fusion of the lipids with the surface of the polymer matrix. The hydrophobic molecules may be any molecules that can drive the self assembly of the lipid shell. Examples of suitable hydrophobic molecules include fatty acids or phospholipid like phosphatidyl ethanolamines or cholesterols. The surface modification of the polymer matrix must not prevent the loading of compounds into the polymer matrix.

The modified polymer matrix may be loaded with the desired compound and stored in a stable dry form. The lipid suspension may also be stored in a dry or lyophilized state. When the lipid vesicle is needed, the dried core and lipid components can be mixed in an aqueous solution and the lipid shell will form on the core. In an alternate embodiment the matrix can be stored dry and can be added to an aqueous liposome suspension to form the lipid vesicle composition.

One embodiment of the method of the invention is shown schematically in FIG. 1. Hydrophobic anchors for the lipid bilayer are created by attaching lipid molecules to the surface of pre-formed polyvinyl alcohol (PVA) xerogel (dry hydrogel) beads. The surface of the modified xerogel is then hydrated and treated with a liposome suspension. Consequently, the hydrophobic lipid molecules and other intrinsic membrane components of the liposomes associate spontaneously with the hydrophobic fatty acid anchors on the surface of the hydrated polymer and self-organize into a distributed membrane over that surface through hydrophobic interactions. Thus not only do these anchors add mechanical stability to the bilayer shell but they also promote its self-assembly. In a sense, these acyl anchors and the polymer to which they are attached act as a cytoskeleton. This self-assembly property allows the bilayer coating to be established on cores ranging in shape from sheets to spheres.

Applications

The lipid vesicles may potentially be useful in several novel biomedical applications. In one application, the vesicles can be used as a drug carrier similar to liposomes. For such an application the vesicles are generally spherical or lipobeads. Lipobeads are expected to be superior to liposomes in the sense of enhanced mechanical stability, controllable size and increased drug loading capability. Long term storage is possible since acylated beads loaded with drug can be stored in a dry form before lipid coating. Also, many of the techniques developed for liposomes such as stimuli sensitive drug release (22), steric stabilization (23) and receptor or antibody mediated drug targeting (7) should still be applicable with lipobeads.

Another application of the lipid vesicles is red cell substitution. In such an application the polymer matrix will be spherical. For hemoglobin (Hb) to perform a conformational change so that oxygen can be released readily at sites of low pO2, encapsulation of Hb with the cofactor, 2,3-DPG is required (6). Combined loading with multiple compounds can be achieved before adding the lipid membrane coating and much less lipid will be needed to entrap a given amount of Hb. By combining the structural features of liposomes and hydrogels, lipobeads may provide a more realistic red cell replacement while at the same time having a much higher encapsulating efficiency than liposomes. Since supported lipid bilayers have been found to create a favorable environment for receptor and enzyme functions (24), lipobeads may also provide a model environment for studying and simulating various biological functions such as cell-cell interactions and the operation of purified and reconstituted trans-membrane proteins such as ion channels and transporters.

In a further application, the lipid vesicles may be used as a vaccine carrier. Vaccines generally comprise small, hydrophilic peptides. The polymer core containing such peptides should have a long shelf life. The lipid bilayer can be selected for a high degree of opsinization thus ensuring recognition by macrophages. Size can be optimized for phagotosis and the hydrogel core can be selected to promote breakdown of the lipid vesicle in the lipid environment of the phagosome.

The lipid vesicle compositions may be delivered to a target site through a variety of known routes of administration including intravenously, intramuscularly and intraperitoneally.

The drug delivery compositions of the invention can be intended for administration to humans or animals. Dosages of the composition will depend on individual needs, on the desired effect and on the chosen route of administration.

The following non-limiting examples are illustrative of the present invention:

EXAMPLES

Example 1

Materials and Methods

PVA was chosen as the hydrogel support because of its proven bio-compatibility (14–15). In addition, PVA can be physically cross-linked (16) so that drugs of large molecular weight can be incorporated into the hydrogel matrix via an absorptive loading process after the beads are made, avoiding exposure to other chemical reagents which might alter the properties of the incorporated drug. Furthermore, the high content of hydroxyl groups of PVA enables the hydrophobic anchor molecules to be covalently attached at a sufficiently high surface density to drive spontaneous assembly of a surface lipid bilayer.

PVA was formed into beads by dispersal in paraffin, freeze-thaw solidification and in situ drying facilitated by bubbling dry air through the suspension. Fully hydrated polyvinyl alcohol (PVA) (Elvanol 71-30, from Dupont) with Mw 116,000 and Mn 39,500 was dissolved in hot water at concentration of 22 w/v % and then dispersed in paraffin oil (Aldrich) containing 1.5 w/v % surfactant (Span 80, Sigma) to form beads. The beads were then cross-linked by slowly freezing the suspension to −20° C. for 12 hrs followed by a slow thaw at room temperature. The beads were then dried by bubbling dry air into the suspension for 1–2 weeks, followed by removal of the oil through re-suspension in hexane, ethyl-acetate and alcohol. This procedure produced Polyvinyl alcohol (PVA) xerogel spheres ranging in size from a few mm to over a hundred mm in diameter. Spherical beads ranging in size from 70 to 90 mm were selected by sieving for further modification.

Surface acylation with fatty acid chains was accomplished by treating the PVA beads with 1M palmitoyl chloride (Aldrich) in hexane at room temperature for 2–3 days. The palmitic species became anchored on the bead via esterification with surface hydroxyls. The completion of this reaction was characterized using attenuated total reflectance (ATR) FTIR and X-ray photoelectron spectroscopy (XPS). With ATR-FITR, the formation of an ester bond was determined, and with XPS, changes in atomic ratio at the surface was measured. For sampling the surfaces with these analytical tools, PVA films were subjected to identical chemical treatment as described above and summarized in FIG. 1. ATR-FITR spectra were recorded on a BIO-RAD-DIGILAB FTS-7 system with a custom designed sample holder with which the polymer films were pressed against a Ge prism (25×5×1 mm with 45° slope of the edge) and XPS spectra recorded on a Leybold MX-200 system with a Mg source, beam energy of 12 KV and beam current of 25 mA. Further details of the surface modification reactions and characterization procedures will be published elsewhere but indicate complete derivatisation of surface hydroxyls with little evidence of penetration beyond 10 nm.

Final formation of lipobeads was accomplished by combining equal parts of a suspension of surface modified beads to a liposome suspension (made by sonicating a 5 mg/ml suspension of phosphatidyl choline until transparent). The hydrophobicity of the acylated bead surface leads to transfer of lipid onto this surface and self-assembly of a bilayer shell around the hydrogel core.

Uniformity, lateral mobility of the supported bilayer were examined using an MRC-500 laser scanning confocal microscope (LSCM) and a fluorescent membrane probe, 7-nitro-2-1,3-benzoxadiazol-4-yl (NBA) labeled dioleoyl phosphatidyl ethanolamine. The LSCM was also used to measure the permeability of the bilayer to ions and fluorescent hydrophilic molecules.

Results

When dried acylated beads are placed in water, their diameter increases about 1.4 times at swelling equilibrium. However, the beads aggregate and float on the water surface due to their surface hydrophobicity. Adding a liposome suspension to the solution with floating beads causes the beads to separate and sink to the bottom. These observations are consistent with contact angle measurements. For acylated PVA surfaces, the observed angle was 103° indicating that the surface is hydrophobic. The contact angle of the surface was reduced to less than 15° after the film was treated with liposomes. When beads are separated from water by filtration and exposed to air, the bilayer is disrupted and the beads again become hydrophobic. The ability to repeatedly form and destroy the bilayer on lipobeads demonstrates their capacity for self-repair.

Measurement of Langmuir-Blodget (LB) film deposition on PVA disks subjected to the same surface modification as lipobeads suggests that a single well-packed lipid layer is formed on the modified surface. For LB deposition, dioleoyl phosphatidyl choline (from Avanti Palar Lipids, and diluted with chloroform to 5 mM prior to use) was spread over the water surface of a LB trough (Mgw Lauda Filmwaage) to form a monolayer with membrane pressure of 30 dyn/cm. When the hydrophobic film is gradually dipped into the water through the monolayer, a layer of lipid is deposited on the film as indicated by the decrease in monolayer surface area. Another layer is deposited when the film is withdrawn but, this second layer is easily stripped from the film surface when the sample is passed back through the monolayer surface, indicating that lipid multi-layers are not formed. The results suggest that the lipobead coating is a bilayer with the interior leaflet anchored by the surface fatty acid residues. The results also illustrate that the bilayer can be anchored on any shape of surface from planar to spherical.

Figure 2:
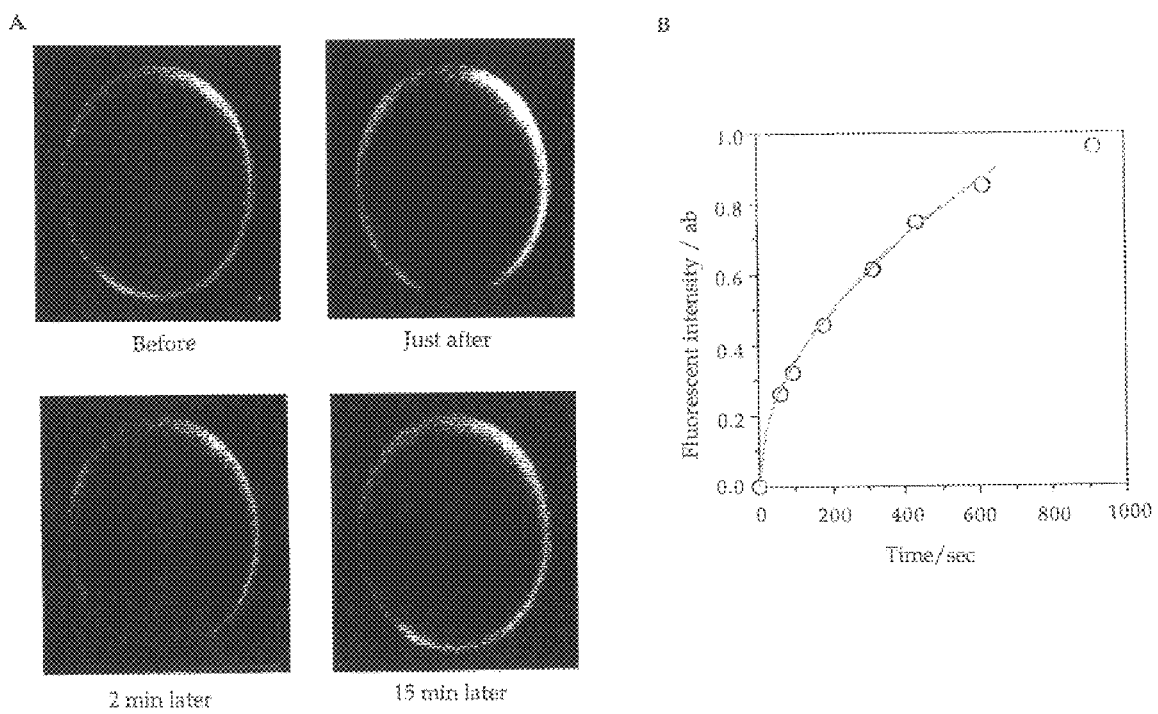
FIG. 2 shows LSCM images of lipobeads treated with fluorescent liposomes.

FIG. 2A show LSCM images of lipobeads treated with liposomes which contained 5% of the fluorescent membrane probe, 7-nitro-2-1,3-benzoxadiazol-4-yl (NBA) labeled dioleoyl phosphatidyl ethanolamine. The continuous ring of fluorescence suggests that following deposition, liposome phospholipid becomes evenly distributed over the lipobead surface. This observation is consistent with the considerable lateral mobility expected for lipid bilayers (17,18). The fluidity of the supported bilayer was tested using a photobleach protocol. The LSCM laser beam was parked over a portion of the bead to induce local photo-bleaching of the fluorescence probe causing an opening in the ring of fluorescence (FIG. 2A). This opening gradually closed over 15 minutes. Since photo-bleach of NBA is irreversible (18,19), this recovery is attributable to the diffusion of labeled lipid molecules through the bilayer into the bleached region. FIG. 2B shows the time course of fluorescence recovery in the bleached area. The solid line is that expected for one dimensional (slab) diffusion of labeled phospholipid from non-bleached area assuming a diffusion coefficient of $1.55 \times 10^{-9}$ cm2/sec. This value is of the same order of magnitude as that estimated for normal lipid bilayers (17,18). One dimensional diffusion was considered because the bleached region produced by the laser is expected to be several fold broader along the z-axis than in the confocal plane.

Figure 3:
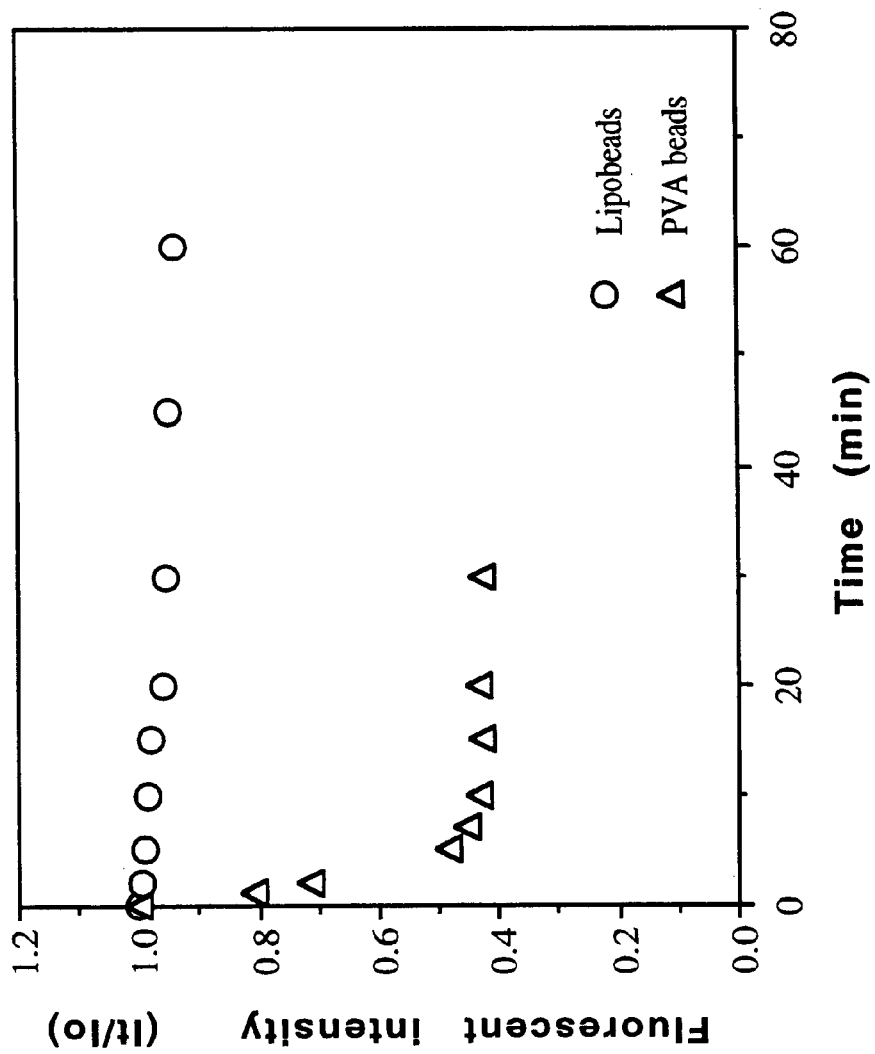
FIG. 3 is a graph showing the fluorescense intensity changes for both lipobeads and bare beads versus time.

The fluorescent dye Lucifer yellow was used as a model compound to test membrane permeability in that its physical-chemical properties are similar to many small, hydrophilic drugs. Both lipobeads and bare PVA beads without hydrophobic surface anchors loaded with Lucifer yellow were added to dye free solution and dye efflux was followed. The fluorescent intensity change for both lipobeads and bare beads after a 5 fold dilution are plotted versus time in FIG. 3. For the bare beads, the loaded Lucifer yellow was rapidly released and reached an equilibrium in a few minutes. With lipobeads however, fluorescent intensity showed little decrease over 60 minutes. It is clear that small hydrophilic molecules can be entrapped in these lipobeads by the lipid coating.

FIG. 4 illustrates the ability of lipobeads to trap ions. The fluorescent indicator dye fluo-3 (Molecular Probes) was used to monitor levels of $Ca^{2+}$ (21) trapped in the core of lipobeads by prior loading. FIG. 4A shows the fluorescence confocal image taken of lipobeads and bare PVA beads loaded with 50 mM fluo-3 in a "$Ca^{2+}$" medium which contained (in mM): 2 $CaCl_2$, 1 EGTA, 5 HEPES, 140 KCl with pH adjusted to 7.4. The bathing solution was diluted 5-fold with a "zero $Ca^{2+}$ medium" identical to the "$Ca^{2+}$" medium except that the $CaCl_2$ was omitted. This 5-fold dilution changes the ratio of $Ca^{2+}$ to EGTA such that extracellular free $Ca^{2+}$ levels should be reduced from 1 mM to 60 nM. With the Lipobeads, the fluorescent intensity of fluo-3 remained constant during the initial 20 minutes of incubation in the low $Ca^{2+}$ medium but quickly decreased after adding a Ca$^{2+}$ ionophore, 4-bromo-A23187 (21) (1/100 dilution (v/v) of 5 mM ionophore dissolved in methanol) to bypass the permeability barrier created by the bilayer coating. Adding the ionophore vehicle (methanol) alone to the same sample caused no change in fluorescent intensity (not shown), excluding possibility that the bilayer membrane was simply disrupted by the solvent. It was concluded that the decrease in fluorescence is due to facilitated Ca$^{2+}$ diffusion across the bilayer membrane mediated by the ionophore. FIG. 4B shows confocal images of bare PVA beads loaded with Ca$^{2+}$ and fluo-3. The same five-fold dilution with "zero Ca$^{2+}$" medium, caused the fluorescence intensity to decrease rapidly in the initial 2 minutes, followed by a more gradual decay (FIG. 4B). These two components of fluorescent decrement may be attributed to the loss of Ca$^{2+}$ and fluo-3, respectively. These results indicate that the lipid coating on the beads provides a permeability barrier to hydrophilic ions such as Ca$^{2+}$.

While the present invention has been described with reference to what are presently considered to be the preferred examples, it is to be understood that the invention is not limited to the disclosed examples. To the contrary, the invention is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety.

Figure Legends

FIG. 1.

Outline of Lipobead Preparation. The surface of preformed polyvinyl alcohol (PVA) xerogel (dry hydrogel) beads is exposed to chloro fatty acids dissolved in hexane which form ester linkages with surface hydroxyls on the xerogel and provide hydrophobic anchors for the bilayer coating. Final formation of lipobeads was accomplished by adding the surface modified beads to a liposome suspension which leads to transfer of lipid onto the acylated surface of the bead and self-assembly of an anchored bilayer shell around the hydrogel core.

FIG. 2.

Lateral mobility in hydrogel supported lipid bilayer labeled with fluorescent phospholipid. A: Confocal images taken before and after a portion of a lipobead surface was photo-bleached. Time of capture is indicated below each image. B: Time course of recovery of fluorescence in the photo-bleached area. The solid line describes the expected recovery based on an earlier time approximation (20) assuming a lipid diffusion coefficient of 1.55×10-9 cm2/s.

FIG. 3.

Release of Lucifer yellow from lipobeads and bare PVA beads. Lucifer yellow was loaded by impregnating acylated and bare PVA beads with a solution of 5 mM Lucifer yellow in 100 mM KCl. Loaded lipobeads, were then formed by liposome treatment. The graph depicts the time course of release of Lucifer yellow from the beads, measured in terms of the decay of fluorescent intensity after a dilution to 1 mM Lucifer yellow.

FIG. 4.

Release of Ca2+ from lipobeads and bare PVA beads loaded with fluo-3. Lipobeads and bare PVA beads loaded with 50 mM fluo-3 in a "Ca$^{2+}$" medium subjected to a five fold dilution with "0 Ca$^{2+}$ medium" which should reduce free extracellular Ca$^{2+}$ to 60 nM. Numbers below the images indicate relative fluorescent intensity. A: Lipid layer on lipobeads prevents Ca$^{2+}$ efflux until an ionophore is added. Images of the same bead before dilution and 20 minutes after dilution, and 2 and 20 minutes after addition of the Ca$^{2+}$ ionophore, 4-bromo-A23187 (5 mM in methanol to reach a final concentration of 50 mM). B: Bare PVA beads do not trap Ca$^{2+}$. Images of a bare bead before dilution and at the times indicated after dilution. Color scale is from 0–250%.

FULL CITATIONS FOR REFERENCES REFERRED TO IN THE SPECIFICATION (1) Rolland, A. (ed.) (1993) Pharmaceutical Particulate Carriers: Therapeutic Applications, Marcel Dekker, New York.
(2) Rogers, J. A. and Choi, Y. W. (1993) Pharm. Res. 10, 913–917.
(3) Ong, S. Liu, H. Qiu, X. Bhat, G. Pidgeon, C. (1995) Anal. Chem. 67, 755–762.
(4) Cai, S. J., McAndrew, C. S., Leonard, B. P., Chapman, K. D. and Pidgeon, C. (1995) J. Chromatogr. A 696, 49–62.
(5) Rothe, U., Aurich, H., Engelhard, H. and Oesterhelt, D. (1990) FEBS Lett. 263, 308–312.
(6) Chang, T. M. S. (1992) Biomat. Art. Cells & Immob. Biotech. 20, 159–179.
(7) Gregoriadis, G. (ed.) (1994) Liposome Technology Vol. 111, 2nd ed., CRC Press, Boca Raton.
(8) Bayer, T. M. and Bloom, M. (1990) Biophys. J., 58, 357–362.
(9) Plant, A. L. (1993) Langmuir, 9, 2764–2767.
(10) Spinke, J., Yang, J., Wolf, H., Liley, M., Ringsdorf, H. and Knoll, W. (1992) Biophys. J., 63, 1667–1671.
(11) Sackman, E. (1996) Science, 271, 43–48.
(12) McConnell, H. M., Watts, T. H. Weis, R. M. and Brian, A. A. (1986) Biochim. Biophys. Acta, 864, 95–106.
(13) Gao, K. and Huang, L. (1987) Biochim. Biophys. Act, 897, 377383.
(14) Tighe, B. J. (1986) in: Hydrogels in Medicine and Pharmacy (Peppas, N. A. ed.) Vol. 111, pp. 53–82, CRC Press, Boca Raton.
(15) Suzuki, M. (1991) in: Polymer Hydrogels, (DeRossi, D., Kajiwara, K., Osada, Y. and Yamauchi, A. eds.) Plenum Press, New York.
(16) Yokoyama, F., Masada, I., Shimanura, K., Ikawa T. & Monoke, K. (1986) Colloid & Polymer Sci. 264, 595–601.
(17) Schmidt, Th., Schutz, C. J., Baumgartner, W., Gruber, H. J. and Schindler, (1996) Proc. Natl. Acad. Sci. 93, 2926–2929.
(18) Almeida, P. F. F., Vaz, W. L. C. and Thompson, T. E. (1992) Biochemistry 31, 7198–7210.
(19) Rosenwald, A. G., Pagano, R. E. and Raviv, Y. (1991) J. Biol. Chem. 266, 9814–9821.
(20) Baker, R. W. Lonsdale, H. K. (1974) in: Controlled Release of Biologically Active Agents (Tanguary, A. C. and Lacey R. E. eds.) pp. 15–22, Plenum Press, New York.
(21) Hernandez-Cruz, A., Sala, F. and Adams, P. R. (1990) Science 247,858.
(22) Nayar, R. and Schroit, A. (1988) in: Liposomes in the Therapy of Infectious Diseases and Cancer (Lopez-Berestein, G. and Fidler, I. J. eds.) pp. 427–440, Alan R. Liss, Inc., New York.
(23) Lasic, D. D. (1994) Ang. Chem. Int. Ed. Engl. 33, 1685–1698.
(24) Plant, A. L., Brighem-Burke, M., Petrella, E. C. and O'Shannessy, D. J. (1995) Anal. Biochem. 226, 342–48.

We claim:

1. A lipid vesicle composition comprising (a) lipid shell attached to (b) a hydrogel polymer matrix having hydrophobic functional groups covalently attached to the surface of the polymer matrix, wherein the lipid shell associates with the hydrophobic functional groups to attach the lipid shell to the polymer matrix.

2. A composition according to claim 1 wherein the polymer matrix is spherical.

3. A composition according to claim 2 wherein the polymer matrix is a hydrogel bead.

4. A composition according to claim 3 wherein the hydrogel polymer matrix having hydrophobic functional groups covalently attached thereto is a polyvinyl alcohol hydrogel.

5. A composition according to claim 1 wherein the hydrogel polymer matrix having hydrophobic functional groups covalently attached thereto is a polyvinyl alcohol hydrogel.

6. A composition according to claim 1 wherein the lipid shell consists of liposomes.

7. A composition according to claim 1 wherein the lipid shell is a bilayer.

8. A method for preparing a lipid vesicle composition comprising:

(a) providing a modified hydrogel polymer matrix having hydrophobic functional groups covalently attached to the surface of the polymer matrix; and (b) mixing the modified polymer matrix with a lipid suspension to form a lipid shell that associates with the hydrophobic functional groups and attaches the lipid shell to the matrix.

9. A method according to claim 8 wherein the hydrophobic functional group is a fatty acid.

10. A method according to claim 8 wherein the polymer matrix is spherical.

11. A method according to claim 10 wherein the polymer matrix is a hydrogel bead.

12. A method according to claim 11 wherein the polymer matrix is a polyvinyl alcohol hydrogel.

13. A method according to claim 8 wherein the polymer matrix is a polyvinyl alcohol hydrogel.

14. A method according to claim 8 wherein the lipid shell consists of liposomes.

15. A method according to claim 8 wherein the lipid shell is a bilayer.

* * * * *